United States Patent [19]

Spencer

[11] Patent Number: 4,488,961
[45] Date of Patent: Dec. 18, 1984

[54] ONE-WAY FILTER UNIT

[75] Inventor: Dudley W. C. Spencer, Wilmington, Del.

[73] Assignee: E. I. Du Pont de Nemours and Company, Wilmington, Del.

[21] Appl. No.: 427,455

[22] Filed: Sep. 29, 1982

[51] Int. Cl.³ .............................................. B01D 35/04
[52] U.S. Cl. .................................... 210/136; 210/390; 604/29
[58] Field of Search ........................ 210/390, 131, 136; 604/29; 55/309

[56] References Cited

U.S. PATENT DOCUMENTS

| 2,992,701 | 7/1961 | White | 55/309 |
|---|---|---|---|
| 3,275,145 | 9/1966 | Jacobellis | 210/390 X |
| 3,545,438 | 12/1970 | DeVries | 128/213 |
| 3,568,977 | 3/1971 | Nelson | 251/148 |
| 3,930,096 | 12/1975 | Gilpatrick | 428/255 |
| 4,111,228 | 9/1978 | Simionescu | 137/512 |
| 4,141,379 | 2/1979 | Manske | 137/496 |
| 4,167,482 | 9/1979 | Muller | 210/68 |
| 4,222,407 | 9/1980 | Ruschke et al. | 137/512.15 |
| 4,239,041 | 12/1980 | Popovich et al. | 128/213 A |
| 4,311,587 | 1/1982 | Hose et al. | 604/29 X |

FOREIGN PATENT DOCUMENTS

| 3001377 | 7/1981 | Fed. Rep. of Germany | 210/927 |
|---|---|---|---|
| 2063684A | 6/1981 | United Kingdom | 604/29 |

Primary Examiner—Frank Spear
Attorney, Agent, or Firm—Scott G. Hallquist

[57] ABSTRACT

A one-way filter for use in fluid filtration comprising a housing having inlet and outlet ports, a filter element or elements, free of mobile fibers or filaments, disposed within said housing, and means within said housing for maintaining the filter element or elements in a filtering position during fluid infusion and in a free-flow position during fluid withdrawal.

6 Claims, 6 Drawing Figures

Legend:
▨ Porous Material.
☐ Microporus Material.

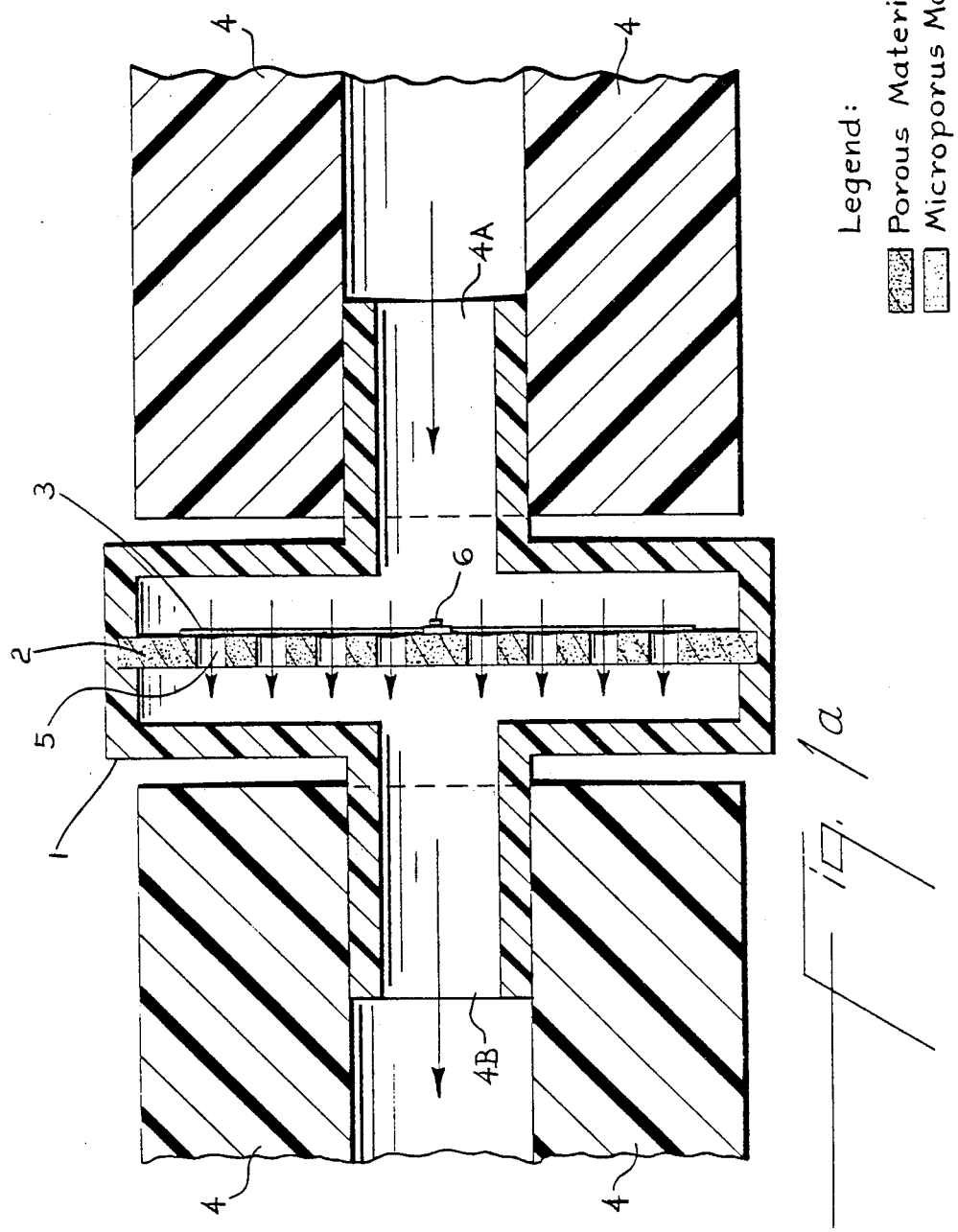

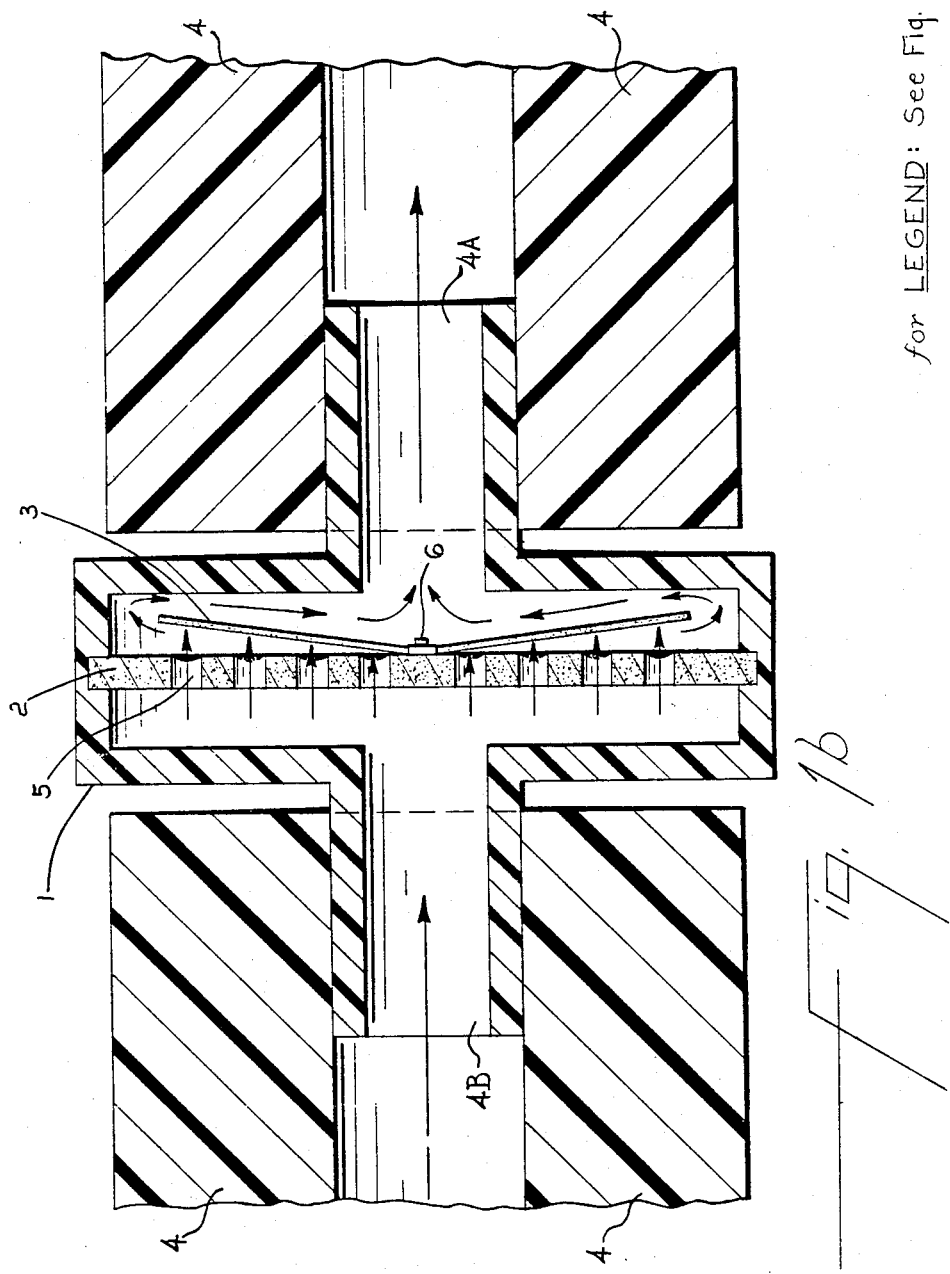

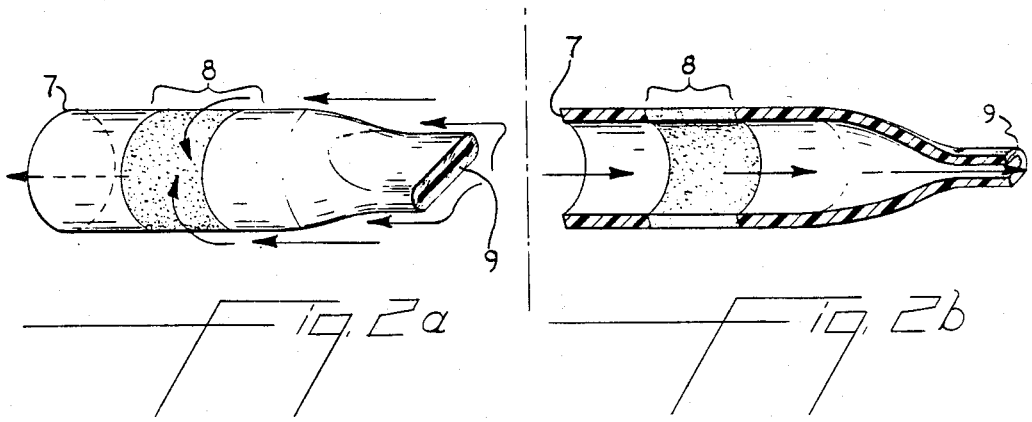
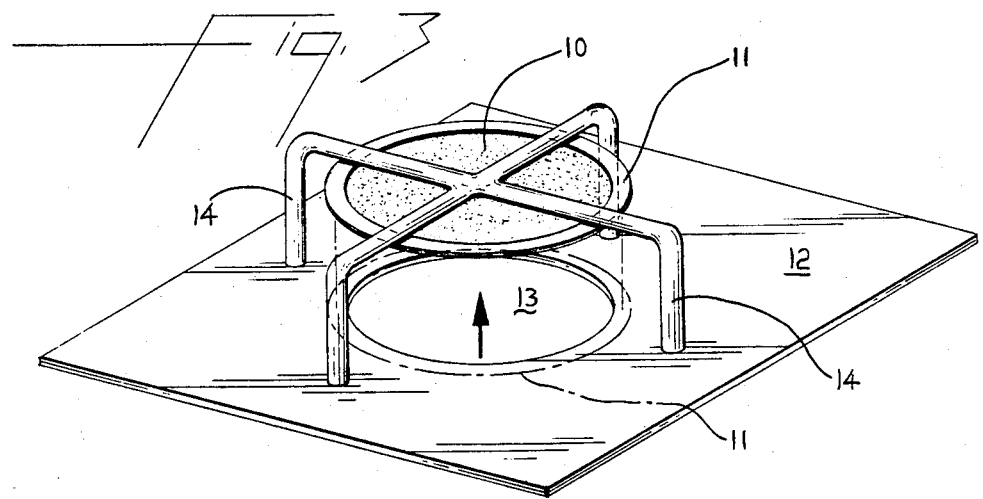
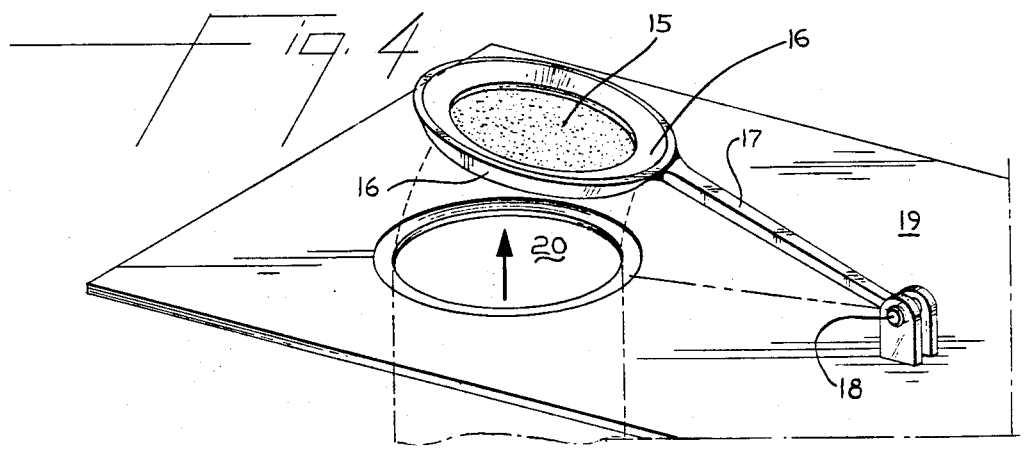

ONE-WAY FILTER UNIT

BACKGROUND OF THE INVENTION

This invention relates to filters for medical devices and, more particularly, to filters adapted to be placed in or along lines or tubes through which fluids are introduced to or withdrawn from the human body during medical treatment.

Many medical procedures involve the administration of fluids to a patient by injection or infusion. Alternatively, a patient's own body fluids may be withdrawn, subjected to treatment outside the body, and returned to the body following treatment. Examples of such procedures include administration of intravenous (I.V.) solutions, hemodialysis, hemoperfusion, peritoneal dialysis, and blood oxygenation. However, a common incident of such treatments is the iatrogenic introduction of contaminating particles into the patient's body. The risks to patient health posed by these particulate contaminants are a matter of increasing concern among health care providers.

A review of the literature on particle contamination by Marlowe, titled "Particles in Medical Devices," (National Technical Information Service PB81-131625, 1980) reports that "mobile particles from any source subject patients to considerable risk of neurological or vascular damage." The Marlowe review notes that contaminating particles originate in a variety of sources, including glass containers, polyvinyl chloride (PVC) connecting tubing, and injectable fluids such as I.V. solutions. Fibers represent one type of frequently encountered particulate contaminant. It is significant that very small particles, such as those which are capable of passing through a filter with a pore diameter of 2 microns ($\mu$m), can cause injury.

One approach to this problem involves the installation of a filter or other screening device in the connecting line between the suspected source of particle contamination and the patient. This approach can be effective. However, in such applications as peritoneal dialysis, in which a fluid is infused into and withdrawn from a body cavity through the same connecting line, a conventional filter is not desirable because it tends to become clogged with cellular and other bodily debris during fluid withdrawal. For example, in peritoneal dialysis, fresh dialysate is infused into a patient's peritoneal cavity where it remains for a time sufficient to permit diffusion and convection of waste materials into the dialysate. After such time, the spent fluid is withdrawn, carrying with it not only the waste materials, but also cellular and other bodily debris from the patient's peritoneal cavity.

Dennehy et al., U.K. Pat. No. 2,063,684, disclose a particle filter on a dialysis line in apparatus for continuous ambulatory peritoneal dialysis (CAPD).

DeVries, U.S. Pat. No. 3,545,438, discloses an apparatus for peritoneal dialysis using unsterilized fresh dialysate. The apparatus includes a filter to remove particles and a second filter to remove bacteria.

In applications such as peritoneal dialysis, the filter can be bypassed during withdrawal by means of a valve-directed shunt. For example, Popovich et al., U.S. Pat. No. 4,239,041, disclose apparatus for continuous ambulatory peritoneal dialysis having a bacterial filter on an inlet line. Between the filter and the entrance to the peritoneal cavity is a valve which can be adjusted to direct fresh dialysate from a reservoir into the peritoneal cavity during infusion, or alternatively, to direct spent dialysate to a collection bag, bypassing the filter.

Valves are undesirable for two reasons. First, valves require that an additional action be undertaken by the operator, frequently a patient. Second, the valve represents an additional inlet or source of bacterial contamination, increasing the risk of patient infection.

Gilpatrick, U.S. Pat. No. 3,930,096, discloses a composite fabric structure which features high resistance to fluid flow in one direction, yet performs a filtration function under conditions of substantially reduced resistance during countercurrent flow. The Gilpatrick device filters fluid flowing in one direction, but substantially checks all flow in the opposing direction.

Muller, U.S. Pat. No. 4,167,482, discloses a filtering apparatus comprising a mop-like filter element relying upon floating or mobile fibers for its effectiveness. Mobile fibrous or filamentous strands are attached to a porous support such that fluid flowing in one direction presses the mobile fibers against the support to form a type of filamentous filter mat. Countercurrent flow mobilizes the strands, freeing them from the mat-like formation, and allows rinsing of the mobilized fibers.

Various one-way valves have been designed which regulate the direction of fluid flow but which do not filter the fluid.

SUMMARY OF THE INVENTION

The invention resides in a one-way filter unit which comprises a housing having inlet and outlet ports, a filter element or elements which are free of mobile fibers or filaments disposed within said housing, and means within said housing for maintaining the filter element or elements in a filtering position during fluid infusion and in a free-flow position during fluid withdrawal.

BRIEF DESCRIPTION OF THE DRAWINGS

FIG. 1a is a cross-sectional view of the one-way filter of the invention in a filtering position.

FIG. 1b is a cross-sectional view of the one-way filter of the invention in a free-flow position.

FIG. 2a is a perspective view of the filter element in a second illustrative embodiment of the invention in a filtering position.

FIG. 2b is a cross-sectional view of the filter element of FIG. 2a, in a free-flow position.

FIG. 3 is a perspective view of the filter element in a third illustrative embodiment of the invention in a free-flow position.

FIG. 4 is a perspective view of the filter element in a fourth illustrative embodiment of the invention in a free-flow position.

DETAILED DESCRIPTION OF THE INVENTION

By "one-way filter" is meant a device which filters fluid flowing in one direction but allows substantially free flow of the fluid when the direction of flow is reversed. As used herein, "filter element or elements free of mobile fibers" refers to elements such as porous membranes, foraminous plates, and various types of isotropic or anisotropic filters, but does not include filter designs which rely upon mobile or floating fibers attached to a porous plate in order to form a filtration mat during fluid flow through the filter. Various means can be employed to maintain the filter element in a filtering position during infusion and in a free-flow position during withdrawal. Several such means, which are activated in response to fluid flow similar to a one-way or check valve, without a need for operator adjustment, are illustrated by the Figures. Pressure additional to that which is required for the fluid to flow into a patient is not necessary. Furthermore, the filter unit can be designed to function whether the patient is sitting, standing or lying down and regardless of the direction of the fluid flow. The housing for the filter unit can be fabricated of a fluid-impermeable, biocompatible material which can be sterilized by conventional means. Examples of such materials include polyethylene, polyvinyl chloride, and polycarbonate.

The filter element in the one-way filter of the invention is a porous membrane or plate, including, for example, a porous frit, or a combination of a porous plate and porous membrane. Selection of the filter element will depend upon the design of the unit selected and upon the size of the particles to be retained, as will become apparent hereinafter. Preferably, the filter element is selected to retain particles of a diameter greater than about 0.5 $\mu$m and, more preferably, greater than about 0.2 $\mu$m. The sizes of the particles retained will depend primarily on pore size. A series of in-line filter units retaining progressively smaller particles may be desirable. Alternatively, a single filter unit can contain a series of two or more one-way filter elements, each successive filter element retaining progressively smaller particles. The material of which the filter element is constructed should not itself shed, or exfoliate, a significant number of contaminating particles. The housing should contain no apertures other than the inlet and outlet ports to preclude the possibility of bacterial contamination.

Referring now to FIG. 1a, the filter unit comprises housing 1 and a filter element comprising porous plate 2 and microporous membrane 3. For the sake of clarity, the size of the pores 5 in porous plate 2 has been greatly exaggerated and their number greatly reduced. Tube ends 4 fit tightly around inlet/outlet ports 4A, 4B which are approximately 6.35 mm (0.25 inch) in outer diameter. The arrows indicate the direction of fluid flow which causes the filter element to be in the illustrated, filtering position. The fluid, such as unused or fresh dialysate, is flowing from a reservoir, not shown, to a patient, not shown. Tube ends 4 can be adhered to housing 1.

In the center of housing 1 is the filter element. Microporous membrane 3 is tacked to porous plate 2 at a particular region, point 6. Porous plate 2 provides support for microporous membrane 3. The pores 5 in plate 2 are large enough to permit flow of cellular and other bodily debris which flow from the patient during withdrawal. A useful pore size is about 100 to 200 $\mu$m.

Microporous membrane 3 is a semi-flexible membrane having pores (not shown) which are less than about 0.2 $\mu$m. The membrane can be, for example, a polycarbonate nucleation track-etched membrane about 10 $\mu$m thick, such as those produced by the methods described by Fleischer, Price, and Walker, Ann. Rev. Nucl. Sci. 15:1 (1965).

Other suitable membrane types include those produced by phase inversion techniques, and can be manufactured from a variety of materials, including nitrocellulose, cellulose ester, nylon, polyvinyl chloride and its copolymers, and polytetrafluoroethylene (PTFE). See Kesting, Synthetic Polymeric Membranes, McGraw-Hill, N.Y. 1971; Scott, ed., Membrane and Ultrafiltration Technology, Noyes Data Corp., Park Ridge, N.J. 1980.

The membrane is tacked, for example, with an adhesive at region 6. Alternatively, the membrane can be tacked nearer an edge of the membrane or along a line on the membrane. Tacking permits the membrane to flex between free-flow and filtering position. When fluid flow is in the illustrated direction, membrane 3 is pushed against plate 2, forcing the fluid to pass through membrane 3.

FIG. 1b illustrates the filter unit of FIG. 1a operating in the free-flow position. Again, the filter unit comprises housing 1 and a filter element further comprising porous plate 2 and microporous membrane 3. As in FIG. 1a, the size of pores 5 has been greatly exaggerated for clarity. The arrows indicate that the direction of fluid flow has been reversed, which causes the filter element to be in the illustrated, free-flow position. The fluid, such as spent dialysate, is flowing from a patient, not shown, to a container for collection, not shown. When fluid flow is in the illustrated direction, membrane 3 is pushed away from plate 2, allowing fluid to pass unimpeded around the edges of membrane 3.

The remaining figures illustrate alternative embodiments of the filter element with means for maintaining the element in a filtering position during infusion and in a free-flow position during withdrawal.

FIGS. 2a and 2b illustrate a tube molded flat at one end. The element is shown in a filtering position in FIG. 2a and in a free-flow position in FIG. 2b. It is fastened to a housing, not shown, at its circular end, region 7. Region 8 comprises a microporous filter. Region 9 is a valve region.

When fluid flow is in the direction indicated by the arrows in FIG. 2a, valve region 9 remains closed, forcing fluid to flow through filter region 8. When fluid flow is in the reverse direction, as illustrated by FIG. 2b, valve region 9 is forced open by the pressure of the fluid, allowing the fluid to bypass filter region 8.

FIG. 3 illustrates a poppet valve-type filter element in a free-flow position. Microporous membrane 10, within supporting gasket 11, is pushed away from support plate 12 by fluid flow through port 13 in the indicated direction, allowing fluid to flow around the membrane. Supporting gasket 11 holds the membrane in a substantially rigid shape. Guide arms 14 maintain the membrane in proper orientation relative to port 13. Fluid flow in the reverse direction pushes membrane 10 towards plate 12. Supporting gasket 11 seals the membrane around port 13, forcing fluid to flow through the membrane.

FIG. 4 illustrates a pivot-type filter element in a free flow position. Microporous membrane 15, within supporting gasket 16, pivots on arm 17 connected to the supporting gasket 16 and to pivot pin 18 on support plate 19. Fluid flows through port 20.

BEST MODE

The best mode contemplated by the inventor for carrying out the invention is illustrated by FIGS. 1a and 1b.

INDUSTRIAL APPLICABILITY

The invention has utility in filtering contaminating particles from fluids being infused into a patient and subsequently withdrawn through the same connecting line.

The above disclosure illustrates particular embodiments of the invention. However, the invention is not limited to the precise construction herein disclosed but rather encompasses all modifications or embodiments thereof within the scope of the following claims.

I claim:

1. A method of performing peritoneal dialysis treatment which comprises the steps of:
    (a) connecting a reservoir of unused dialysate to a one-way filter unit comprising a housing having inlet and outlet ports, a filter element or elements free of mobile fibers disposed within said housing, and responsive means within said housing for maintaining the filter element or elements in a filtering position during dialysis infusion and in free-flow position during dialysate withdrawal, said responsive means being activated by fluid flow during both dialysate infusion and dialysate withdrawal;
    (b) transmitting unused dialysate from said reservoir into said housing;
    (c) filtering the unused dialysate by passing the unused dialysate through the filter element or elements within said housing, said filter element or elements being maintained in filtering position during dialysate infusion;
    (d) introducing the filtered, unused dialysate into the peritoneal cavity of a patient;
    (e) retaining the dialysate in the peritoneal cavity of the peritoneal dialysis patient for a preselected residence time;
    (f) connecting the one-way filter unit to a container for collection of spent dialysate;
    (g) withdrawing spent dialysate from the peritoneal cavity of the patient;
    (h) transmitting the spent dialysate from the peritoneal cavity of the patient to the housing;
    (i) passing the spent dialysate through said housing and bypassing said filter element or elements, said filter element or elements being maintained in free-flow position during dialysate withdrawal; and
    (j) transmitting the spent dialysate to said container for the collection of spent dialysate.

2. A one-way filter unit for filtering unused dialysate during infusion thereof into the peritoneal cavity of a pertioneal dialysis patient, which filter unit comprises
    (a) a housing having two inlet/outlet ports, one inlet/outlet port adapted for connection to a reservoir of unused dialysate or a container for collection of used dialysate, and the other inlet/outlet port adapted for connection to the patient's peritoneal cavity;
    (b) a porous support plate disposed transversely to dialysate flow within said housing; and
    (c) a flexible membrane filter element or elements attached in a flexible region to the porous support plate, such that the filter element or elements are maintained in a filtering position during transmission of unused dialysate from the reservoir through said housing and into the patient's peritoneal cavity, and in a free-flow position during during transmission of dialysate from the patient's peritoneal cavity through the filter unit to a container for the collection of used dialysate.

3. Filter unit of claim 2 wherein the filter element or elements retain particles larger than about 0.5 μm.

4. Filter unit of claim 3 wherein the filter element or elements retain particles larger than about 0.2 μm.

5. Filter unit of claim 2 wherein at least two membrane filter elements attached to porous support plates are disposed within said housing between the inlet/outlet ports.

6. Filter unit of claim 5 wherein each of said filter elements retains particles of a size range which differs from the size range of particles retained by the other filter element or elements.

* * * * *